United States Patent [19]

Kitrell

[11] 4,297,999
[45] Nov. 3, 1981

[54] PORTABLE RESUSCITATION APPARATUS

[76] Inventor: John V. Kitrell, 1740 Yolande, Lincoln, Nebr. 68521

[21] Appl. No.: 59,079

[22] Filed: Jul. 19, 1979

[51] Int. Cl.³ .......................................... A61M 16/00
[52] U.S. Cl. ................................. 128/205.16; 128/28; 128/205.23; 128/205.25
[58] Field of Search ................ 128/28, 204.21, 205.16, 128/205.13, 205.23, 30.2, 204.23, 205.25, 202.13, 204.22, 205.18, 206.24, 206.28, 207.11; 35/17

[56] References Cited

U.S. PATENT DOCUMENTS

| 2,376,871 | 5/1945 | Fink | 128/206.28 X |
| 3,073,301 | 1/1963 | Hay et al. | 128/205.25 X |
| 3,343,535 | 9/1967 | Lytle et al. | 128/206.24 |
| 3,613,677 | 10/1971 | Blasko | 128/204.21 |
| 4,196,725 | 4/1980 | Gunderson | 128/205.25 |

FOREIGN PATENT DOCUMENTS

| 1533196 | 7/1968 | France | 128/205.13 |
| 37712 | 3/1936 | Netherlands | 128/206.24 |
| 428338 | 5/1935 | United Kingdom | 128/206.24 |

Primary Examiner—Henry J. Recla

Attorney, Agent, or Firm—Zarley, McKee, Thomte, Voorhees & Sease

[57] ABSTRACT

A portable resuscitation apparatus is described including a flat support having a neck cushion at one end thereof to properly position the patient's head and to also provide a secure means for attaching a mask to the patient's face and head. The mask includes a pair of cheek straps extending therefrom which are secured to opposite sides of the neck cushion. A flexible strap is secured to the upper central portion of the mask and to the neck cushion. A flexible hose extends from the mask to a ventilation pump mounted on the support whereby compression of the pump will cause air to be forced through the flexible hose to the mask. The mask includes a first valve provided therein which permits communication from the atmosphere of the interior of the mask during the times that the pump is not being operated. The mask also includes a second valve which is vented to the atmosphere upon a predetermined pressure being reached within the mask. A source of oxygen is in communication with the flexible hose so that the ventilation pump will supply pure oxygen to the patient during the initial portion of the ventilating action. An electronic rhythm unit is mounted on the support for indicating the prescribed beat for proper closed chest massage and ventilation.

3 Claims, 12 Drawing Figures

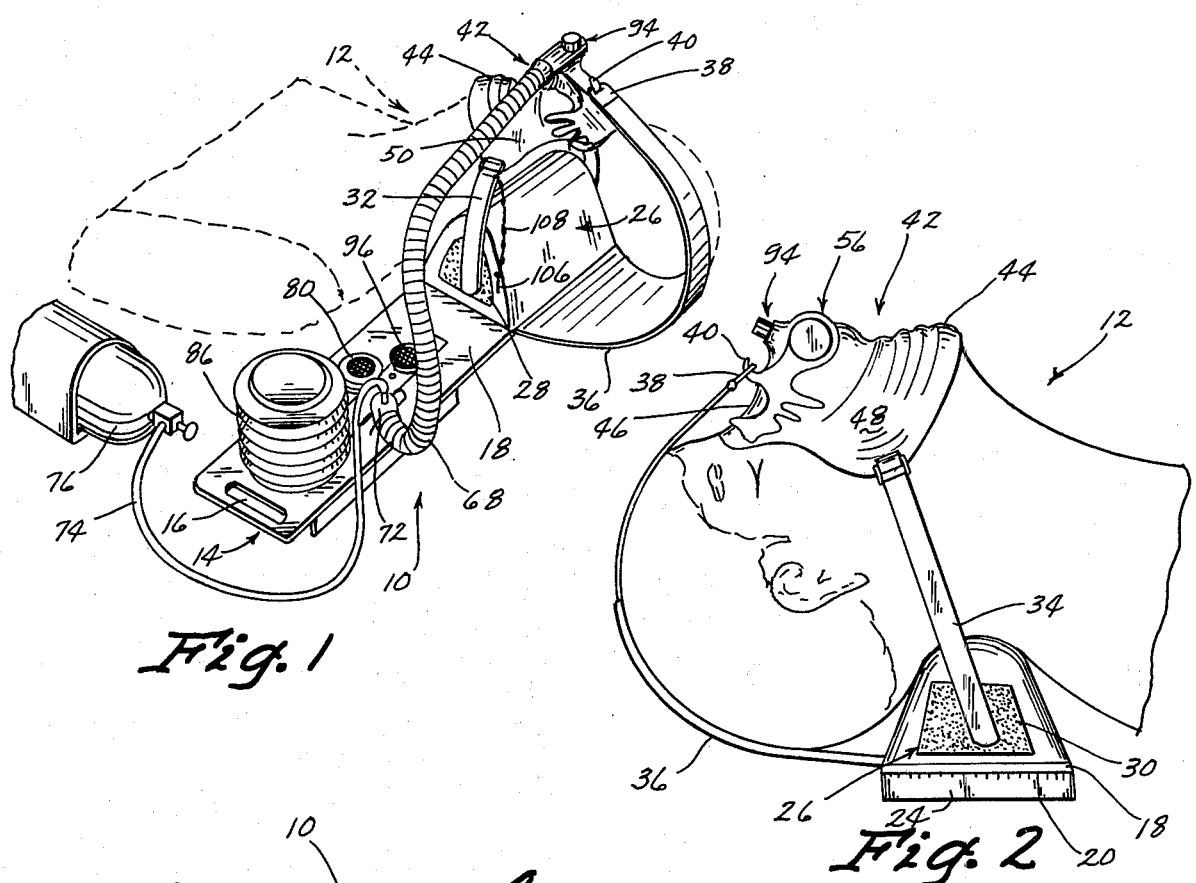
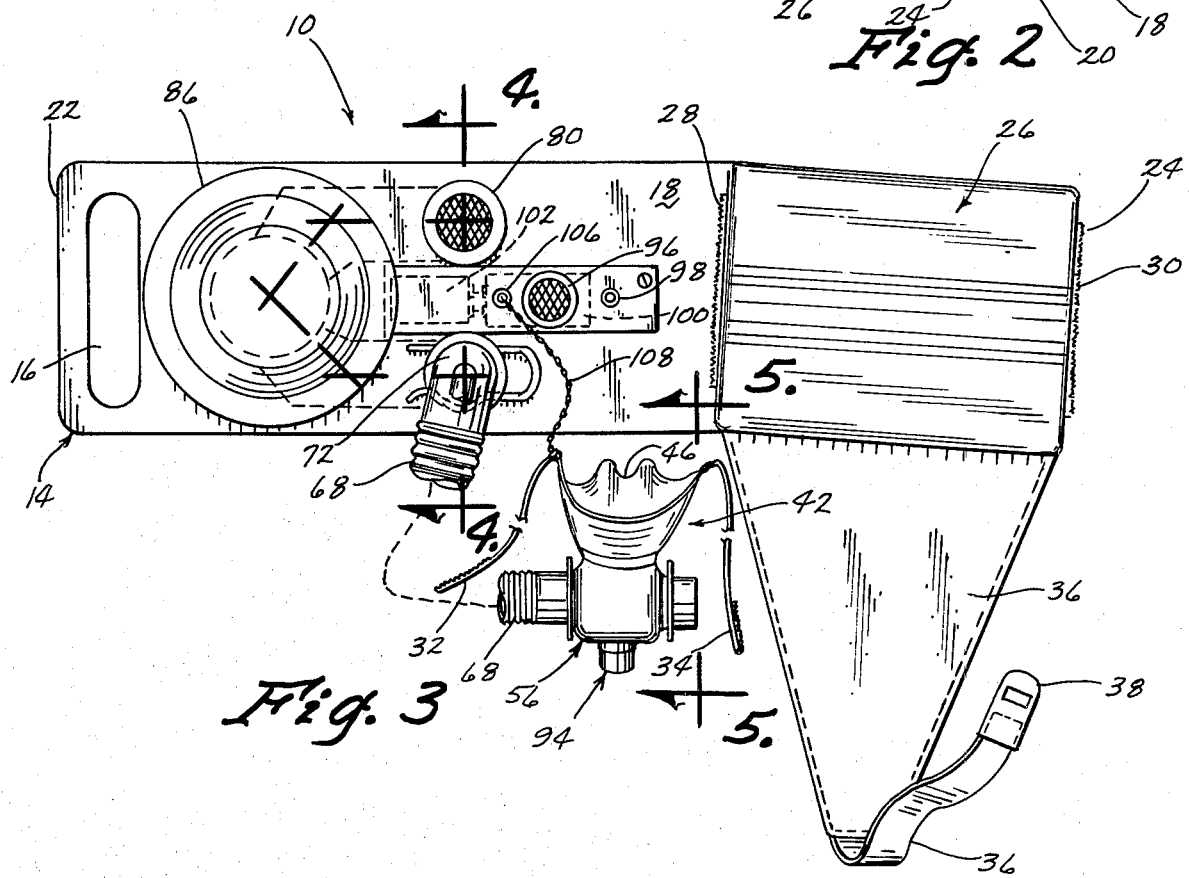

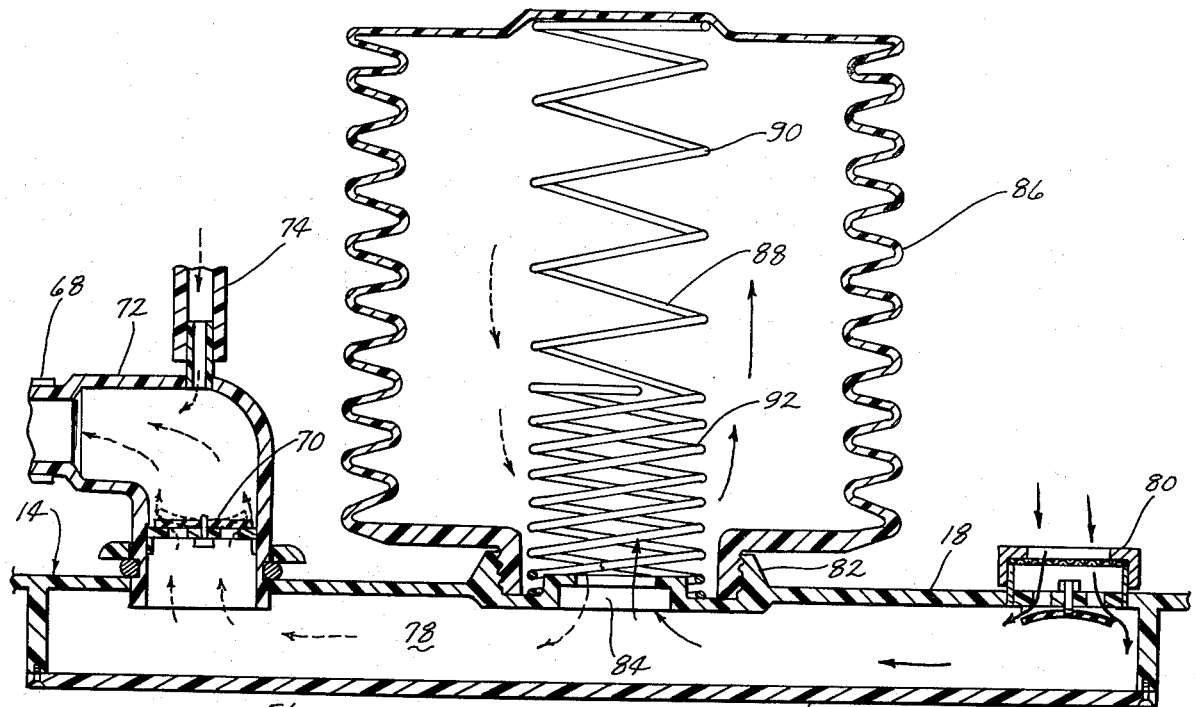
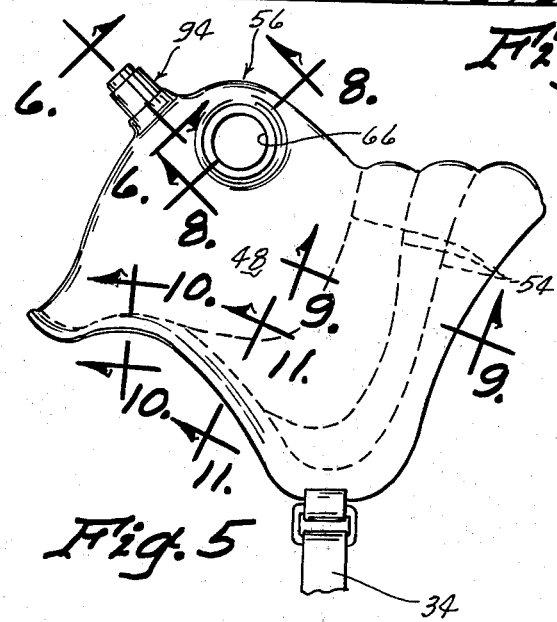
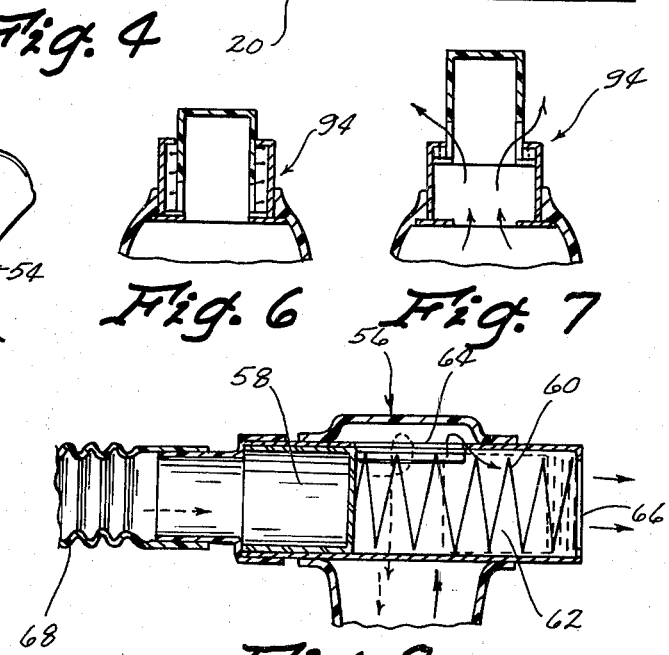
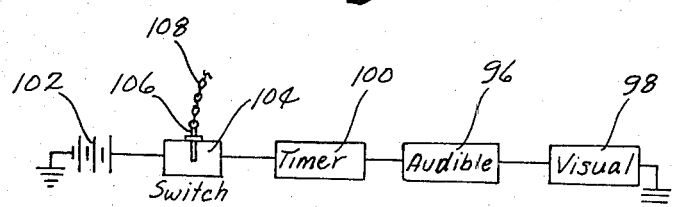

PORTABLE RESUSCITATION APPARATUS

BACKGROUND OF THE INVENTION

Cardio-pulmonary resuscitation is a procedure commonly given to heart attack victims in an attempt to restore the heart beat and breathing of the victim. In CPR techniques, the chest of the victim is normally compressed five times or strokes with the lungs of the victim then being ventilated for one stroke or time. The compression and ventilation strokes are then repeated.

Portable resuscitation units have been previously provided but to the best of applicant's knowledge, none of the portable resuscitation units include an electronic rhythm apparatus mounted thereon for indicating the proper sequence or timing of the compression and ventilation strokes which is extremely critical. Additionally, the portable resuscitation units presently available are not believed to have means associated therewith for properly positioning the victim's head so that the victim's air passageways are clear for facilitating the introduction of oxygen and/or air to the patient's lungs. Further, the previous resuscitation units include masks which do not necessarily fit all victims.

Therefore, it is a principal object of the invention to provide a portable resuscitation unit which may be used by persons who are unskilled in CPR techniques.

A further object of the invention is to provide a portable resuscitation unit including a neck cushion which properly positions the victim's head and provides a means of attaching the mask to the patient's head or facial area.

A still further object of the invention is to provide a portable resuscitation unit including a ventilation pump to provide pressure ventilation during the cardio-pulmonary resuscitation.

A still further object of the invention is to provide a portable resuscitation unit including an electronic rhythm unit having a prescribed beat for proper closed chest massage rhythm which is enunciated in both an audible tone and a visual light.

A still further object of the invention is to provide a resuscitation unit including an oxygen supply and a ventilation pump so that pure oxygen is initially supplied to the patient's upper bronchi area during the ventilation stroke.

A still further object of the invention is to provide a portable resuscitation unit which includes a pressure mask which has a relief valve provided thereon which vents the interior of the mask to the atmosphere upon a predetermined pressure being reached within the mask.

A still further object of the invention is to provide a pressure mask for a portable resuscitation unit which insures that a proper fit will be achieved on the patient's facial area.

A still further object of the invention is to provide a pressure mask for a portable resuscitation unit which permits communication between the interior of the mask and the atmosphere during the times that the ventilation stroke is not occurring.

A further object of the invention is to provide combined elements of a cardio-pulmonary resuscitator to permit one person to administer proper CPR to a victim for a reasonable period of time without the physical demand encountered by other known methods.

BRIEF DESCRIPTION OF THE DRAWINGS

FIG. 1 is a perspective view of the apparatus being employed on a victim who is illustrated in broken line:

FIG. 2 is an end view of the apparatus:

FIG. 3 is a partial top view of the apparatus:

FIG. 4 is an enlarged sectional view seen on lines 4—4 of FIG. 3:

FIG. 5 is a side view of the pressure mask of this invention:

FIG. 6 is an enlarged sectional view seen on lines 6—6 of FIG. 5:

FIG. 7 is a view similar to FIG. 6 except that the valve is illustrated in an open condition:

FIG. 8 is an enlarged sectional view seen on lines 8—8 of FIG. 5:

FIG. 9 is an enlarged sectional view seen on lines 9—9 of FIG. 5:

FIG. 10 is a sectional view seen on lines 10—10 of FIG. 5:

FIG. 11 is a sectional view seen on lines 11—11 of FIG. 5; and

FIG. 12 is a schematic of the rhythm unit of this invention.

SUMMARY OF THE INVENTION

A portable resuscitation unit is provided which includes means for cushioning the victim's head and for properly positioning the victim's head so that the air passageways of the victim are open to receive air and/or oxygen. A pressure mask is included in the unit and has a first valve provided therein which permits communication between the interior of the mask and the atmosphere during the times that the ventilating pump is not being employed. A second valve is also provided in the mask to provide communication from the interior of the mask to the atmosphere should a predetermined pressure be reached within the mask. Connection means is provided on the mask for attachment to the neck cushion so that the mask will be securely held onto the facial area of the victim. A flexible hose extends from the mask and is in communication with a bellows pump which may be compressed so as to force air and/or oxygen to the mask. A source of oxygen is in communication with the flexible hose so that pure oxygen is initially supplied to the upper bronchi of the victim during the compression stroke of the bellows pump. An electronic rhythm unit is provided on the apparatus which visually and automatically indicates the proper beat for the closed chest heart massage and for the ventilation stroke.

DESCRIPTION OF THE PREFERRED EMBODIMENT

The resuscitator apparatus of this invention is referred to generally by the reference numeral 10 while the numeral 12 refers to a victim requiring cardio-pulmonary resuscitation. Apparatus 10 includes a support means or base 14 having handle opening 16 at one end thereof for carrying purposes. For purposes of description, base 14 will be described as comprising a top portion 18, bottom portion 20 and opposite ends 22 and 24. A cushioned neck support 26 is mounted on one end of base 14 and is designed to support the victim's neck area in the manner illustrated in FIG. 2 so that the victim's air passageways will be clear or open to facilitate resuscitation. Support 26 is provided with Velcro fastening elements 28 and 30 at its opposite sides which are adapted to detachably receive the ends of the straps 32 and 34 which are provided with compatible Velcro fastening elements. Strap 36 is secured to support 26 and extends therefrom as illustrated in FIGS. 1 and 2. As seen, strap 36 is designed to extend over the victim's head and is provided with a connector 38 at the end thereof which is adapted to be removably secured to the hook 40 on mask 42.

Mask 42 is comprised of a flexible plastic or rubber material and includes a chin receiving area 44, nose receiving area 46 and opposite sides 48 and 50 designed to fit over the victim's cheeks. The interior surface of mask 42 is provided with elongated and spaced apart ridges 54 which are designed to engage the face of the victim to insure a seal between the mask and the victim's face regardless of the configuration or size of the victim's facial area.

Mask 42 is provided with a normally open breathing valve 56 which is in communication with the interior of the mask and the atmosphere. Valve 56 includes a piston or valve member 58 slidably mounted in chamber 62 which is urged to the position of FIg. 8 by spring 60. When valve member 58 is in the position of FIG. 8, atmospheric air is supplied to the interior of the mask inasmuch as chamber 62 is in communication with the interior of the mask through opening 64 and is in communication with the atmosphere through opening 66. When air pressure is supplied to valve member 58 from hose 68, the valve member 58 moves to the right as viewed in FIG. 8 to seal opening 66 thereby preventing ambient or atmospheric air from entering the mask through opening 66 and to prevent the air which is supplied to the mask from hose 68 from passing into the atmosphere. When valve member 58 seals opening 66, air from hose 68 is supplied to the interior of the mask.

The other end of hose 68 is provided with a chamber valve 70 in fitting 72 which permits the air to pass therethrough in the direction depicted by arrows in FIG. 4. Fitting 72 is in communication with a hose 74 which extends from a source of pressurized oxygen 76. Fitting 72 is mounted on base 14 and communicates with air passageway 78 formed in base 14. A one-way ambient air inlet valve 80 is mounted on base 14 (FIG. 4) and communicates with air passageway 78 to permit ambient air to enter passageway 78.

Base 14 has a threaded neck portion 82 which extends around opening 84 and which threadably receives the bellows or ventilation pump 86 thereon. Pump 86 is moveable from the normal expanded position to a compressed position. Two-stage spring 88 is positioned in pump 86 for yieldably resisting the compression of pump 86. Spring 88 includes stages 90 and 92. The preferred total capacity of pump 86 is 900 cubic centimeters. It is preferred that the relationship of spring 88 and pump 86 is such that only the resistance of spring stage 90 is encountered for the first 500 cubic centimeters of compression with the spring stages 90 and 92 resisting compression of the final 400 cubic centimeters of the pump. In practice, the pump 86 is only compressed until the resistance of stage 92 is encountered since 500 cubic centimeters is approximately the recommended volume of air to be supplied to the victim during each ventilation stroke. If additional air is needed beyond the first 500 cubic centimeters, the pump 86 is further compressed against the added resistance of stage 92 to supply the needed air to the mask.

During the compression stroke, air is forced from the interior of pump 86, through opening 84, passageway 78, valve 70, hose 68, valve 56 and into the mask 42. During the expansion stroke of the pump, ambient air is drawn inwardly through valve 80 into passageway 78 and into the interior of pump 86 through opening 84.

A normally closed exhaust 94 is mounted on mask 42 and is designed to open upon a predetermined pressure being experienced within the mask to prevent undue air pressure being supplied to the victim.

The apparatus is provided with an electronic rhythm unit including an audible signal 96 and a visible signal 98 connected to timer 100 and battery 102. A normally closed switch 104 is imposed in the circuit of FIG. 12 and is kept in the open position by a removable pin 106. Pin 106 has a flexible chain or the like 108 connected thereto which is connected to the mask 42 so that the mask 42 will pull the pin 106 from the switch 104, when the mask is placed on the patient, to energize the audible and visual signals so that the proper beat will be indicated to assist the attendant in the cardio-pulmonary technique. For example, the time would energize the audible and visual signals so that the apparatus indicates the sequence and timing of the ventilation strokes as well as the compression strokes for the chest area.

The fact that the oxygen supply 76 is in communication with the hose 68 insures that an accumulation of pure oxygen will be collected in the hose between ventilation strokes. When a ventilation stroke is made on the pump, the valve member 58 on the mask closes so that the oxygen is supplied to the interior of the mask. The victim's chest and lungs are normally at rest when the ventilation action begins and have neither positive or negative air pressure. Therefore, the oxygen displaced by the pump pressure will enter the victim's nose, windpipe and larger bronchi first followed by additional air until maximum pressure for lung inflation reaches the prescribed limits. It is believed that this particular system of ventilation has the beneficial effect of putting the highest level of oxygen into the small lung bronchi area which have the closest relationship for oxygenating the heart blood.

The configuration of the mask is such that it will readily adapt to the victim's facial area with the ridges 54 insuring contact between the interior of the mask and the facial area so that a positive seal will be provided therebetween to insure that the proper supply of air and/or oxygen will be supplied to the patient.

It should be noted that valve 94 serves to indicate that the mask is pressurizing but upon reaching a predetermined safe limit pressure, valve 94 exhausts surplus air through the ports as indicated by arrows in FIG. 7.

Thus it can be seen that the apparatus of this invention accomplishes at least all of its stated objectives.

I claim:
1. A portable resuscitation apparatus, comprising,
a portable support means having top and bottom portions,
a support member extending upwardly from said support means adapted to support the patient's neck to position the patient's head for resuscitation,
a manually operated air supply means mounted on said support means,
a flexible mask means having an air inlet supply base extending therefrom which is in operative communication with said air supply means,
and connector means for detachably connecting said mask means to the patient's face and to maintain the patient on said support member, said air supply means comprising a flexible bellows pump mounted on said support means, said support means having a first air passageway formed therein which is in communication with said pump, said base being in communication with said air passageway whereby compression of said flexible bellows pump will supply air to said mask means, said bellows pump being movable between compressed and extended positions, a spring means in said bellows pump for yieldably resisting the compression of said bellows pump and for moving said bellows pump from its compressed position to its extended position, said spring means being of the two-stage type so that said spring means will yieldably resist, at a first predetermined rate, the compression of said bellows pump during a predetermined initial portion of its compression stroke and will yieldably resist, at a rate greater than said first predetermined rate, during a predetermined portion of its compression stroke after said initial portion.

2. A portable resuscitation apparatus, comprising, a portable support means having top and bottom portions, a support member extending upwardly from said support means adapted to support the patient's neck to position the patient's head for resuscitation, a manually operated air supply means mounted on said support means, a flexible mask means having an air inlet supply base extending therefrom which is in operative communication with said air supply means, and connector means for detachably connecting said mask means to the patient's face and to maintain the patient on said support member, an audible signal means mounted on said support means for signaling the sequence of cardio and pulmonary resuscitation, said signal means being battery operated and being controlled by a switch; control means normally maintaining said switch in its open position, and means connecting said mask means and said control means for closing said switch to actuate said signal means when said mask means is donned on the patient.

3. The apparatus of claim 2 wherein a visual signal means is also provided on said support means which is coordinated with said audible signal means.

* * * * *